United States Patent
Brown

(10) Patent No.: US 6,260,022 B1
(45) Date of Patent: *Jul. 10, 2001

(54) MODULAR MICROPROCESSOR-BASED DIAGNOSTIC MEASUREMENT APPARATUS AND METHOD FOR PSYCHOLOGICAL CONDITIONS

(75) Inventor: Stephen James Brown, Palo Alto, CA (US)

(73) Assignee: Health Hero Network, Inc., Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/237,546

(22) Filed: Jan. 26, 1999

Related U.S. Application Data

(63) Continuation of application No. 09/127,404, filed on Jul. 31, 1998, now Pat. No. 5,940,801, which is a continuation of application No. 08/843,495, filed on Apr. 16, 1997, now Pat. No. 5,828,943, which is a continuation of application No. 08/682,385, filed on Jul. 17, 1996, now abandoned, which is a continuation of application No. 08/479,570, filed on Jun. 7, 1995, now abandoned, which is a continuation of application No. 08/233,674, filed on Apr. 26, 1994, now abandoned.

(51) Int. Cl.[7] .................................................. G06F 17/60
(52) U.S. Cl. ................................................................ 705/2
(58) Field of Search ................................. 377/16; 705/1, 705/2

(56) References Cited

U.S. PATENT DOCUMENTS

| 3,811,116 | * | 5/1974 | Takeuchi et al. | 600/437 |
| 3,883,235 | * | 5/1975 | Lynn et al. | 351/246 |
| 4,060,915 | * | 12/1977 | Conway | 434/307 R |

(List continued on next page.)

FOREIGN PATENT DOCUMENTS

WO 97/37738  10/1997  (WO).

OTHER PUBLICATIONS

Gardner, et al.; "Comprehension and Appreciation of Humorous Material Following Brain Damage"; *Brain*; Sep. 1975; 98(3); p. 399–412; Dialog: File 153, Acc#02859983.*

Bruce, et al.; "The Effects of Sympathic Nervous System Activation and Psychological Stress . . . "; *Diabetologia*; 35(9); 1992; 835–843; Dialog: File 5, Acc#9629427.*

Furnham, et al.; "Measuring Locus of Control: a Critique of General, Children's, Health–and Work–related Locus of Control Questionaires"; *British Journal of Psychology*; v84 n4; p443(37); Nov. 1993; Dialog: File 88, Acc#14903135.*

(List continued on next page.)

*Primary Examiner*—Edward R. Cosimano
(74) *Attorney, Agent, or Firm*—Black Lowe & Graham PLLC

(57) ABSTRACT

A modular system for diagnostic assessment of psychological conditions which employs a compact microprocessor-based unit such as a video game. In accordance with the invention, the microprocessor-based unit is programmed to produce a video display that prompts a patient or user to interactively operate one or more switches. Information recorded during an interactive diagnostic assessment procedure is analyzed to provide a doctor or other health care professional with information that is helpful to determine whether clinical therapy and/or medication may be required. The disclosed embodiment of the invention relates to diagnostic assessment of Attention Deficit Hyperactivity Disorder and Attention Deficit Disorder with a game-like video display being used to obtain a measure of various neuropsychologic indicia of attention.

2 Claims, 10 Drawing Sheets

U.S. PATENT DOCUMENTS

| | | | | |
|---|---|---|---|---|
| 4,518,361 | * | 5/1985 | Conway | 434/307 R |
| 4,730,253 | * | 3/1988 | Gordon | 434/335 |
| 4,803,625 | * | 2/1989 | Fu et al. | 600/483 |
| 4,894,777 | * | 1/1990 | Negishi et al. | 600/558 |
| 4,931,934 | * | 6/1990 | Snyder | 434/236 |
| 4,978,303 | * | 12/1990 | Lampbell | 434/258 |
| 5,219,322 | * | 6/1993 | Weathers | 600/27 |
| 5,230,629 | * | 7/1993 | Buschke | 434/236 |
| 5,262,943 | * | 11/1993 | Thibado et al. | 600/300 |
| 5,295,491 | | 3/1994 | Gevins | 128/731 |
| 5,307,263 | * | 4/1994 | Brown | 600/301 |
| 5,335,338 | * | 8/1994 | Proesel | 395/500 |
| 5,344,324 | * | 9/1994 | O'Donnell et al. | 434/258 |
| 5,381,195 | * | 1/1995 | Rootzen et al. | 351/222 |
| 5,678,571 | * | 10/1997 | Brown | 128/898 |
| 5,828,943 | * | 10/1998 | Brown | 434/258 |
| 5,868,683 | * | 2/1999 | Protopapas et al. | 600/559 |
| 5,899,855 | * | 5/1999 | Brown | 600/301 |
| 5,940,801 | * | 8/1999 | Brown | 705/2 |

OTHER PUBLICATIONS

Villa, et al.; "A Structured Pictorial Questionaire to Assess DSM–III–R–based Diagnosis in Children (6–11 years)"; *Journal of Abnormal Child Psychology*; v22 n4; p.403(21); Aug. 1994; Dialog: File 88, Acc#15759542.*

Dialog Abstract: File 155, Acc#03534751; Kennedy et al.; "Television Computer Games: A 'New Look' in Performance Testing"; *Aviat Space Environ Med*; Jan. 1982, 53(1); p. 49–53.*

Adilman; "Videogames: Knowing the Score"; *Creative Computing*; v9; p224(5); Dec., 1983; Dialog: File 148, Acc#01891055.*

Mims; "Psychological Testing"; *Computers & Electronics*; v23; p22(6); Feb., 1985; Dialog: File 47, Acc#02654858.*

Klintberg et al: "Exploring the connections between platelet monamine oxidase activity and behavior relationships with performance in neuropsychological tasks"; Neuropsychology 23 (4) 1990–1991, pp. 188–196, (abstract only).*

McCullagh, PJ et al., "Computerised Paradigms for Eliciting the Contingent Negative Variation Event–Related Potential," Proceedings of the Annual International Conference of the Engineering in Medicine & Biology Society, IEEE, Conf. 14, pp. 2481–2483 (Oct., 1992).

Copy of International Search Report mailed 12/9/99.

* cited by examiner

MODULAR MICROPROCESSOR-BASED DIAGNOSTIC MEASUREMENT APPARATUS AND METHOD FOR PSYCHOLOGICAL CONDITIONS

This application is a continuation of prior application Ser. No. 09/127,404, now U.S. Pat. No. 5,940,801, filed Jul. 31, 1998, which is a continuation of prior application Ser. No. 08/843,495, now U.S. Pat. No. 5,828,943, filed Apr. 16, 1997, which is a file wrapper continuation of application Ser. No. 08/682,385, filed Jul. 17, 1996, now abandoned, which is a file wrapper continuation of prior application Ser. No. 08/479,570, filed Jun. 7, 1995, now abandoned, which is a file wrapper continuation of prior application Ser. No. 08/233,674, filed Apr. 26, 1994, now abandoned, priority from the filing date of which is hereby claimed under 35 U.S.C.§ 120, and all of which are hereby incorporated by reference.

FIELD OF THE INVENTION

This invention relates to apparatus and methods for diagnostic assessment of psychological conditions that enable a patient or user to collect important diagnostic measures of psychological conditions or behavior for transmittal to and analysis by a health care professional.

BACKGROUND OF THE INVENTION

The traditional method of diagnosing and assessing psychological conditions involves periodic clinical sessions in which a clinician attempts to obtain insights of a patient's condition by conducting interviews and, in some cases, conducting tests. This traditional method of psychological testing and evaluation is often very lengthy and, as a result, costly. Moreover, many psychological conditions and behavior patterns are not easily diagnosed during a series of routine clinical visits because the condition or behavior is situation-dependent and, thus, may not be observable in a clinical setting. Further, the manifestations or behavior patterns of certain disorders are heterogeneous in nature, which complicates identification and diagnosis. Specifically, where a high degree of heterogeneity is present, standardized and normalized diagnostic measures intended to identify a particular or preferred regimen of therapy often do not exist. Under such conditions, the identification and diagnosis of a psychological condition or behavior pattern becomes very subjective, often resulting in an even larger number of diagnostic clinical sessions and higher costs. Lower rates of diagnostic accuracy and efficacy also result.

Many people suffering from psychological disorders are unable to obtain clinical assistance because of the high cost of diagnosis and treatment. Further, even where cost is not of a major deterrent, many people lose confidence in the clinical procedure and cease attending clinical sessions when diagnostic assessment becomes difficult and lengthy. Difficulties can be encountered even by patients that persevere. Between their periodic clinical visits, they usually are left on their own with no encouragement or treatment.

Advances in the various fields of electronics and telecommunications have had a significant impact on medical diagnostic and monitoring equipment, including the development of devices that can be used in the home or other non-clinical settings. Recent advancement with respect to self-care health monitoring of afflictions such as diabetes are set forth in my co-pending patent application Ser. No. 07/977,323, filed Nov. 17, 1992, now U.S. Pat. No. 5,307,263 which is entitled "MODULAR MICROPROCESSOR-BASED HEALTH MONITORING SYSTEM."

Some experiments and trials have been conducted with respect to incorporating computers and similar electronic equipment in arrangements for psychological testing and assessment that is performed in a clinical setting. Very recently, some experiments and trials have been conducted in which a patient uses a microprocessor device such as a "palm-top computer" to record behavioral information between clinical sessions and, in some cases, for limited therapeutic purposes. However, adoption of modern microprocessor and communication technology to diagnosing, monitoring or treating psychological disorders has not progressed at the same rate as technological advances in areas of medicine that relate to physiological conditions.

There are numerous reasons why microprocessors and modern communication techniques have not been widely applied to devices for psychological diagnoses, evaluation or treatment. As previously mentioned, the behavior attendant many psychological disorders is situation dependent. Thus, to be useful, a device must be relatively small, relatively easy to use and unobtrusive so that a patient or subject can use the device in an appropriate environment and is comfortable with using the device in that environment. Cost and efficacy are also important factors if use of the device is to result in a reduction in the professional time and other costs associated with diagnosis and treatment of various psychological conditions.

In order to provide a diagnostic tool that can be used in settings other than clinical sessions, other criteria should be met. For example, provision should be made for a clinician or other health care professional to easily acquire data gathered by the diagnostic tool and to analyze that data. Further, to achieve optimum utilization, the diagnostic tool should be extremely versatile, lending itself to adaptation to the assessment of various psychological conditions. Preferably, the device should be adaptable enough to allow a clinician to establish diagnostic routines suited for various species of the same general psychological disorder of even for a particular individual. Versatility sufficient for use of the device in at least limited monitoring and therapeutic procedures is also desirable.

For all of the above reasons, a need exists for improved methods and apparatus for psychological evaluation and assessment. This is especially true with disorders such as depression, anxiety, schizophrenia, addiction, eating disorders, attention deficit disorders, attention deficit and hyperactivity disorder, and other psychological and behavioral problems which are highly stimulus-dependent (i.e., may be manifested primarily or only in situations that are difficult to synthesize in a clinical environment). The extreme heterogeneity of these psychological conditions has complicated diagnosis and treatment, a drawback that leaves many adults and children with chronic conditions that are handicaps both from the social and economic standpoint.

Providing reliable and accurate tests for diagnosing psychological disorders in children has been a substantial problem. In particular, prevalent childhood psychological disorders such as Attention Deficit Hyperactivity Disorder and Attention Deficit Disorder are difficult to assess because attention is a multi-construct neuropsychological process that includes sustained attention (vigilance) and selective attention (i.e., the ability to maintain attention in the presence of distractions and the ability to appropriately shift attention). Children with Attention Deficit Disorder and Attention Deficit and Hyperactivity Disorder are often impulsive, requiring a relatively high degree of motivation in order to complete tasks that employ cognitive skills appropriate to their particular age group. Moreover, current assessment tests for Attention Deficit Disorder and Attention Deficit Hyperactivity Disorder are relatively subjective, and even when effectively administered, basically provide only an evaluation of whether a child exhibits a deficit in his or her ability to focus and maintain attention. That is, current tests have been successful only in identifying a large heterogeneous group that exhibit the basic symptoms of Attention Deficit Hyperactivity Disorder. Little success has been obtained relative to assessing the degree of neuropsychologic mechanism impairment. Thus, current diagnostic techniques do not identify homogeneous subgroups of children having Attention Deficit Hyperactivity Disorder, which is needed in order to prescribe and administer effective therapy.

Developing diagnostic and therapeutic tools for psychological assessment and treatment of children is especially challenging. To obtain essential, unbiased information for diagnosis of Attention Deficit Hyperactivity Disorder or Attention Deficit Disorder, a child being tested must be at ease and must be motivated since children with these disorders are easily distracted when faced with situations requiring continued attention and/or routine, relatively tedious tasks. Thus, if cognitive tests are employed, they must be appealing to younger children, but not leave older children bored and unmotivated to perform well. Otherwise, test results will be skewed and diagnosis made even more difficult.

SUMMARY OF THE INVENTION

This invention addresses the previously discussed need for new and useful apparatus and methods for diagnostic assessment of psychological conditions, providing a valuable adjunct and supplementation to traditional clinical assessment. Apparatus arranged in accordance with the invention is extremely versatile, being suitable for use in diagnostic assessment of various psychological conditions and being especially well suited for assessment of conditions that affect children such as Attention Deficit Disorder and Attention Deficit Hyperactivity Disorder. The invention also is extremely versatile in that it is suited for use in a clinical setting as well as use in remote locations such as the home, school, or workplace.

Basically, apparatus configured in accordance with the invention includes a programmable microprocessor unit that is responsive to program instructions that are supplied by an external source. In the disclosed embodiment, a receptacle is included in the programmable microprocessor-based unit for receiving an external ("removable/insertable") memory unit which includes a digital storage medium for storing program instructions that control operation of the programmable microprocessor-based unit. In other embodiments, the program instruction instructions can be transferred to memory circuits of the microprocessor-based unit by various digital data transmission systems and techniques.

The programmable microprocessor-based unit also includes circuitry for generating a video display in accordance with program instructions stored in an internal memory of the microprocessor-based unit and/or the digital storage medium of the external memory unit. In the operation of the invention, the displayed video signals interactively prompt a patient or user to operate one or more switches that are located on the microprocessor-based unit. Preferably, the programmable microprocessor-based unit also includes a sound generator operable for producing selected tones, single words or simple phrases of simulated speech, simple musical passages, and other sounds appropriate to the video display during the operation of the microprocessor-based unit.

In the currently preferred embodiments of the invention, the microprocessor-based unit is a compact video game system, with the program instructions being provided by an external memory unit that corresponds to a game cartridge. The invention can employ either a handheld video game such as the compact video game system manufactured by Nintendo of America Inc. under the trademark "GAME BOY," or less compact video game systems such as the "SUPER NES" video game, which also is marketed by Nintendo of America Inc. As is well known, handheld video games of the type mentioned are unitary devices that include a display screen and control switches for operating the video game. On the other hand, the larger video game systems operate in conjunction with a television set or video monitor and consist of a console unit, which receives a game cartridge, and one or more controllers, which include at least a portion of the switches for operating the video game system. Use of either type of video game system has several general advantages, including the widespread availability and low cost of such systems. Further, such systems provide an easy-to-use, unobtrusive device that can be used either in a clinical setting or other environment such as the home, school, or workplace. Moreover, the video display can be structured to provide motivation for a patient or user and, in at least some instances, the same or an additional program cartridge can provide appropriate educational or therapeutic video displays and processes.

Use of the video game system for the programmable microprocessor-based unit of the invention is especially advantageous with children because of the popularity and widespread acceptance of all types of video games. In accordance with the invention, video and audio sequences are preferably presented in game-like format with animation that is suitable for children or other selected age groups.

Regardless of whether a video game system is employed, the programmable microprocessor-based unit can be used to analyze the data obtained during a diagnostic assessment procedure. In some cases, a full analysis will be performed so that the information that is transmitted or returned to a clinician is in a final form. In other situations, partial (or even no) analysis of gathered diagnostic information is performed by the programmable microprocessor-based unit. In those situations, partial (or full) analysis is performed at the clinician's facility or, alternatively, at a facility that gathers information for analysis and subsequent relay to the clinician.

Systems that are arranged in accordance with the invention include two components in addition to the above-discussed programmable microprocessor-based unit: (1) a programmable digital signal processor; and, (2) a communication link for allowing signal transmission between the programmable microprocessor-based unit and the programmable digital signal processor. In some arrangements of the invention, the programmable digital signal processor is a personal computer that is located at the clinic or other facility of the health care professional. In these arrangements, the programmable microprocessor-based unit can be located at the clinician's facility with the communication link for coupling signals between the programmable microprocessor-based unit and the clinician's computer being an electrical cable that provides a RS232 communication link or some other digital signal transmission arrangement. However, a primary advantage of the invention is use of the microprocessor-based unit at a location that is remote from the clinician's facility (e.g., use between clinical sessions in an environment appropriate to assessment of the psychological condition of interest). At least two basic types of communication links allow assessment of the psychological condition to be made at a subject's home or other location that is remote from the clinician's facility.

First, an RS232 serial data port or other means for coupling digital signals to the central processing unit of the clinician's personal computer can be connected to a cable that is adapted for receiving an external memory unit (e.g., memory cartridge) that is used with the programmable microprocessor-based unit to gather assessment data. In such an arrangement, the external memory unit is interconnected with the clinician's computer to access stored signals that represent information gathered during a diagnostic assessment procedure that was performed earlier at a subject's home or other suitable location. In many situations, the clinician's computer will have been previously interconnected with the external memory unit to allow the clinician to establish stored program instructions that will implement a desired diagnostic assessment procedure when the patient or user operates the microprocessor-based unit in conjunction with the memory unit.

The second type of communication link that allows the diagnostic assessment procedure to be conducted at a location other than the clinician's facility involves the use of various types of signal transmission media. For example, the digital data signal processor (e.g., personal computer) employed by the clinician can include an external or internal modem for receiving and transmitting digital signals via the various types of conventional telephone systems. Likewise, a modem and associated conventional data management circuitry can be either included in or interconnected with the microprocessor-based unit to allow information gathered during a diagnostic assessment procedure to be transmitted to the clinician for review and analysis. In some cases, it may also be advantageous to use the data transmission link for remote programming of the user's external memory unit, thereby permitting changes to be made in the diagnostic procedure of a particular patient or user without a visit to the clinician's office.

Transmission media other than a telephone system can be used for coupling signals between a clinician's digital data processing system and a remotely located programmable microprocessor-based unit that is used for diagnostic assessment of psychological conditions. For example, recently developed interactive audio/visual systems using coaxial cable or optical fiber can be employed as well as other types of digital networks that provide information services and communication between users. In some of these arrangements, the digital data signal processor need not be located at the clinician's facility. That is, the invention can be implemented so that the digital signal processor is a clearinghouse that in effect functions as a central server that is capable of functioning with a relatively large number of programmable microprocessor units and, in addition, capable of serving the needs of at least several clinicians. In these arrangements, the clearinghouse digital signal processor collects and stores diagnostic assessment information transmitted to the clearinghouse from any number of programmable microprocessor-based units. Information is then provided to the appropriate clinician or clinical facility by facsimile or data transmission techniques. Alternatively, the information can be printed and delivered to the appropriate clinician.

The disclosed embodiments of the invention are configured and programmed for diagnostic assessment of Attention Deficit Disorder and Attention Deficit Hyperactivity Disorder. The currently preferred realizations of the disclosed embodiment allow a clinician to selectively configure sequences of tests ("tasks") that fall into the two basic categories: delay reaction tasks and performance-paced continuous performance tasks. During a delay reaction task, the programmable microprocessor-based unit operates to first generate an audible and/or visual warning signal to alert the user that the microprocessor-based unit will soon produce an audio, visual, or audiovisual target stimulus. When the target stimulus is produced, the user or patient responds by activating a switch or control of the microprocessor-used unit. Preferably, the time between the warning stimulus and the target stimulus within a predetermined range that is selected by the clinician, with each particular time delay being randomly selected through programmed operation of the microprocessor-based unit. For each delayed reaction task, a signal is generated indicating whether the user reacted to the target stimulus and, if so, the time that elapsed between generation of the target stimulus and the user's operation of the selected switch. Collecting and storing the user's reaction times for a sequence of delayed reaction tasks allows subsequent analysis by the system digital data processor to obtain information such as a record of reaction time versus time delay, the user's best (fastest) reaction time, the user's mean reaction time, and/or the standard deviation of reaction times. In some situations, it may also be advantageous to store the delayed reaction task information so that analysis can be performed that allows the detection of trends such as whether the user's reaction time generally increased or decreased as the sequence of delayed reaction tasks progressed. Such information may indicate an increase or decrease in attention level with time.

In the currently preferred realizations of the disclosed embodiment of the invention, the visual delayed reaction task includes the display of a car, the model of which selected by the user prior to initiation of the diagnostic procedure. The car is shown at a starting line with a traffic signal having a red, yellow, and green light being prominently displayed in the foreground. Initially, the red light is illuminated, a warning signal is then provided to the user by illuminating the yellow light and, when the microprocessor-selected time delay has elapsed, the green light is illuminated to provide the target stimuli. In the currently preferred realizations of the disclosed embodiments of the invention, the words "ready . . . set . . . go" are synthesized by the sound generator of the microprocessor-based unit.

During the continuous performance tasks, the system user observes the system display while target stimuli pass across it. The object is for the user to activate a switch or control of the microprocessor-based unit when target stimuli are at a predetermined location on the display. For example, in the currently preferred realizations of the disclosed embodiments of the invention, the previously mentioned car is displayed so that it appears to be passing by trees that are located along the side of a road. The target stimulus is a specified type of fruit (e.g., an orange, apple, lemon, or cluster of grapes) on the tree. The object is for the user to activate the switch or control of the microprocessor-based unit when a predetermined stimulus appears (e.g., an apple). When the switch or control is activated a hand and arm move upwardly from the car and, if the switch is timely activated, the fruit is captured. When the user correctly identifies and captures a target stimulus, the time interval between appearance of target stimuli is decreased by a predetermined amount. On the other hand, if the user does not properly respond to a target stimulus, the time interval between target stimuli is increased.

During the conduction of a sequence of continuous performance tasks, information is recorded to reflect the number of target stimuli correctly identified, the number of target stimuli missed, the number of responses to non-target stimuli, the number of correct, but delayed, responses, and the final interstimulus time interval.

Audio continuous performance tasks are also provided wherein the user is to respond to certain audio signals while ignoring others. For example, in the currently preferred realizations of the disclosed embodiments, the car shown on the system display unit is passing along a dark road with a small portion of the road passing under the car's headlights. A low frequency "radar beep" is sounded for each non-target stimulus, and a high frequency radar beep is sounded to represent the target stimulus. Although the display is relatively dark, the bases of the trees can be seen and when the user properly responds to a target stimulus, a hand swings upwardly from the car to catch the fruit.

The battery of tests provided by the currently preferred embodiments of the invention also include continuous performance tasks with various distractions. For example, in the above-discussed realization in which the user activates a switch or control of the microprocessor-based unit to catch a predetermined type of fruit as a car passes across the system display, moving objects such as hopping frogs, fluttering butterflies, and flying saucers are periodically and randomly displayed. In the audio continuous performance tasks, the distractions consist of synthesized speech such as "Now!" or "Go!." During sequences of continuous performance tasks that include distractions, the number of distractions that cause user reaction are recorded as well as the information recorded during continuous performance task sequences that do not include distractions.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
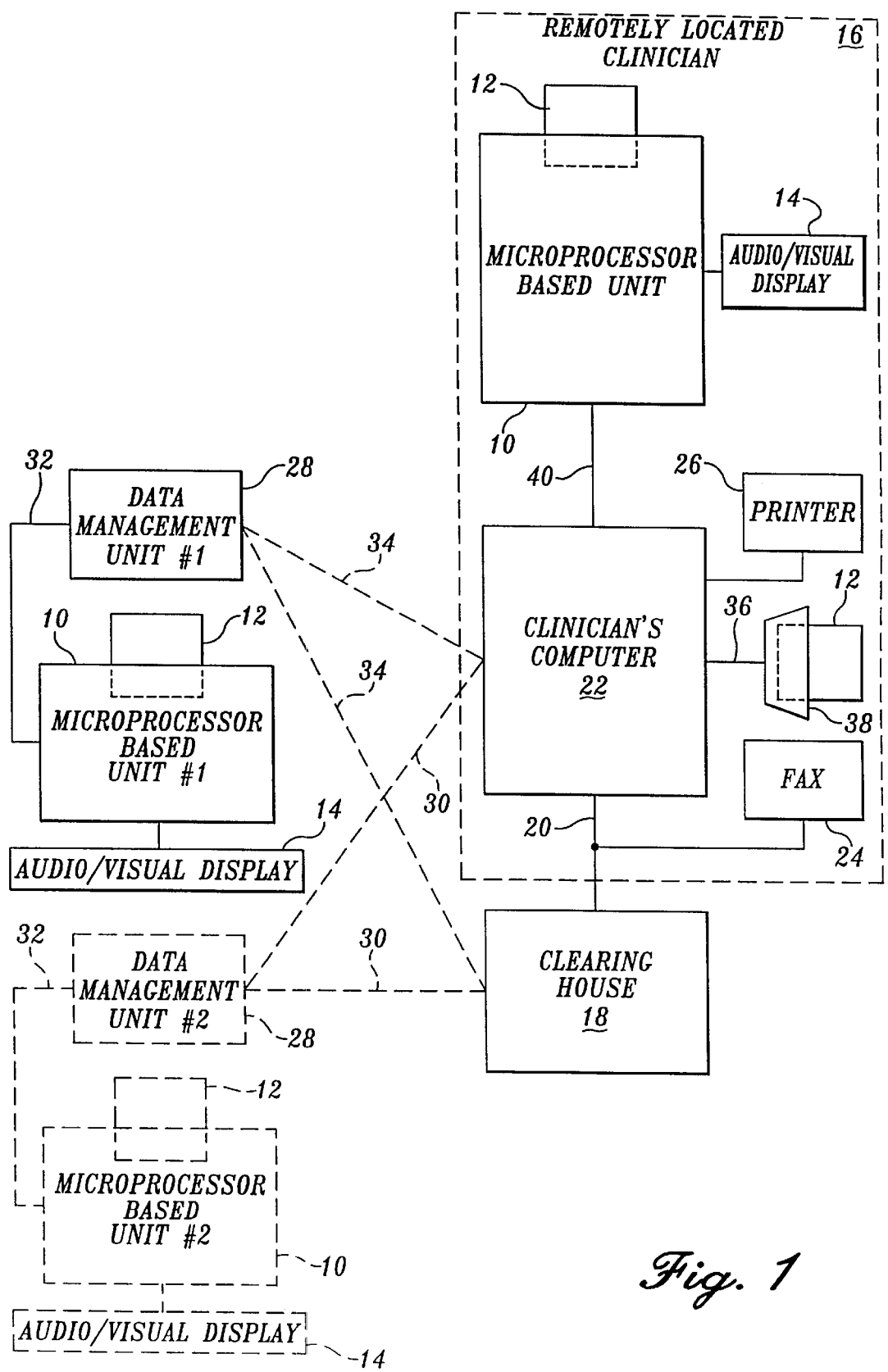
FIG. 1 is a block diagram that illustrates a psychological diagnostic measurement system of this invention, depicting microprocessor-based patient units connected in signal communication with a clinician's computer system and/or a clearinghouse for collection and analysis of diagnostic data originating with a large number of patient units.

FIG. 1 illustrates one embodiment of a diagnostic measurement system configured in accordance with the invention. The depicted embodiment includes a programmable microprocessor-based unit 10 that includes a receptacle for receiving an external memory unit 12, which can be easily inserted and removed from microprocessor-based unit 10. Removable memory unit 12 includes a digital storage medium for storing program instructions that control the operation of microprocessor-based unit 10 and, in addition, allows storage of diagnostic test information that is generated during operation of microprocessor-based unit 10 for diagnostic assessment of a psychological condition.

Various storage media known to those skilled in the art can be used as the digital storage medium of external memory unit 12. For example, conventional read-only memory (ROM) can be employed for storage of program instructions that are not changed or altered when external memory 12 is reconfigured for a different patient or reconfigured for measurements relating to a different type of psychological condition. Optically scanned memory such as currently available compact disc memory can also be employed. In addition, various types of erasable read-only memory and random access memory (RAM) having a battery back-up can be used to provide a storage medium for program instructions that may be changed when external memory 12 is configured for use with a different patient or for the diagnostic assessment of the different psychological condition. Erasable read-only memory or battery backed-up RAM also can be used for storage of information gathered when microprocessor-based unit 10 is operated to gather diagnostic measurement information that relates to one or more psychological conditions. Moreover, in newly developing technologies such as audio/video interactive television and networks for digital communications program instructions can be transmitted to microprocessor-based unit 10 and stored in random access memory.

As is indicated in FIG. 1, microprocessor-based unit 10 is interconnected with an audio/visual display unit 14. During operation of the invention for diagnostic assessment of psychological conditions, microprocessor-based unit 10 generates audio and video signals that are presented to the patient or system user by audio/visual display unit 14. The audio/visual presentation is controlled by program instructions that are either stored in external memory 12 or are otherwise supplied to microprocessor-based unit 10. In the disclosed embodiments, the visual presentation is structured to elicit responses from the user of microprocessor-based unit 10 (e.g., a patient or research subject) that provide that diagnostic measures relating to a particular psychological condition. In that regard, the embodiments disclosed herein are arranged for diagnostic assessment of Attention Deficit Hyperactivity Disorder and Attention Deficit Disorder. Upon understanding the operation of the invention and the various manners in which it can be configured, it will be recognized that the invention can be used in the diagnoses of various other psychological conditions and behavior patterns, including anxiety disorders, depression, schizophrenia, addiction, and weight control/eating disorders.

A primary advantage of the invention is the ability to conduct a diagnostic assessment procedure in an environment other than the office of a clinician or other health care facility. This particular aspect of the invention can be important with respect to diagnosing psychological conditions that are highly situation-dependent. Further, since it is not necessary for a clinician to be present when a diagnostic assessment procedure is executed, the costs of diagnoses and treatment is reduced. For example, during a clinical session, a clinician can instruct a patient or subject in the use of the invention for diagnostic assessment of a particular psychological condition. The patient or user then uses microprocessor-based unit 10, a suitably programmed external memory 12, and an audio/visual display unit 14 between clinical sessions to gather appropriate diagnostic measurements while the subject is in suitable environmental surroundings (e.g., at home, school, or the workplace). Information gathered during the diagnostic assessment is then made available to the clinician for consideration and analysis.

There are two basic ways in which information that relates to the results of the diagnostic assessment can be conveyed to a clinician or other person who serves as an administrator for the conduction of the diagnostic assessment. These same techniques are employed for establishing the diagnostic procedure (i.e., storing suitable program instructions in external memory 12). The first technique for transferring test results or programming microprocessor-based unit 10 (e.g., external memory unit 12) involves data transmission between microprocessor-based unit 10 and a remotely located clinician's office (or other health care facility) or, alternatively, a remotely located facility that stores the information for subsequent analysis and transmission to the clinician. In the second technique, microprocessor-based unit 10 (or external memory unit 12) is physically transferred between the site at which the diagnostic assessment is made and the clinician's facility or other remote location.

With respect to the first information transfer technique, FIG. 1 schematically illustrates arrangement of the invention for remote exchange of data and information between a microprocessor-based unit 10 and either a remotely located clinician 16, or a clearinghouse 18. In such an arrangement, clearinghouse 18 includes one or more digital signal processors and associated peripheral equipment (e.g., printers, signal storage media, facsimile facilities) sufficient for gathering diagnostic measurement information from a relatively large number of microprocessor-based diagnostic tools (represented by microprocessor-based unit number 1 and microprocessor-based unit number 2 of FIG. 1). A communication link 20 is shown in FIG. 1 between clearinghouse 18 and the clinician's remote location 16 to indicate transfer of information electronically or by other signal transmission means. Specifically, data and information can be transferred electronically between clearinghouse 18 and a clinician by various conventional data transmission systems, including those implemented through telephony, transmission of radio frequency signals, modulated coherent light, etc. As is indicated in FIG. 1, the signals sent by clearinghouse 18 to the clinician's facility 16 can be coupled to devices such as the clinician's computer 22 and/or the clinician's facsimile machine 24. Signals transmitted to the clinician's computer 22 can be stored with or without additional processing. In the same regard, analytical signal processing of the diagnostic assessment data gathered by microprocessor-based unit can be performed at various stages of information transmission between patient and clinician. For example, data processing can be performed in microprocessor-based unit 10, the clinician's computer 22, clearinghouse 18 and/or the hereinafter described data management unit 28. In any case, when the diagnostic information is transmitted to the clinician's facility, it can be displayed on a display unit of the clinician's computer 22 (not shown in FIG. 1); printed by a printer 26 that is connected to computer 22; or processed by other devices that are peripheral to the clinician's computer 22.

With continued reference to the embodiment of the invention shown in FIG. 1, signals representative of information gathered during a diagnostic assessment procedure (and other signals appropriate to system operation) are coupled to (or from) clearinghouse 18 and microprocessor-based diagnostic unit 10 via a data management unit 28 and a communication link 30. Like communication link 20, which provides signal transfer between clearinghouse 18 and the clinician's facility 16, communication link 30 can be of several different types. In some instances, communication link 30 will be a signal path established by a telephone system. Alternatively, RF signal transmission can be employed. Communication link 30 also can be established through the use of specialized digital networks, including recently developed interactive audio/video systems such as those operated in conjunction with cable television.

In the arrangement of FIG. 1, each depicted data management unit 28 is interconnected with its associated microprocessor-based unit 10 by a cable 32 that includes electrical conductors for carrying signals between the two units. In each arrangement of the invention, data management unit 28 provides the signal processing that is necessary for interfacing microprocessor-based unit 10 with communications link 30 and/or a communications link 34. Communications link 34 provides for transmission of signals between microprocessor-based unit 10 and the clinician's remote location 16 (e.g., coupling of signals to and from the clinician's computer 22). Like the previously discussed communication links 20 and 30, communication link 34 can be realized in a variety of ways.

Because of the wide range of communication links 30 and 34 that are available for practice of the invention, data management 28 will take on various forms and configurations. For example, in an arrangement of the invention in which communications link 30 and/or 34 is a signal path established by a conventional telephone system, data management unit 28 will include a modem and will operate to perform the signal processing necessary to transmit information to clearinghouse 18 and/or the clinician's remote location 16. In some arrangements of the invention, the signal processing required for modem data transmission will be implemented by a microprocessor unit that is incorporated in data management unit 28. In other situations, the microprocessor of microprocessor-based unit 10 can be employed to perform the signal processing necessary for modem signal transmission. Similarly, the hardware associated with modem transmission (e.g., telephone line connection) can be included in data management unit 28 or incorporated in microprocessor-based unit 10.

FIG. 1 also indicates one manner in which the invention can be employed for remote administration of diagnostic assessment of psychological conditions without the need for data management unit 28 and communication links 30 and 34. In particular, in the arrangement of FIG. 1, an external memory unit 12 can be inserted in a receptacle 38 that electrically connects external memory unit 12 to the clinician's computer 22 via a cable 36. With an external memory 12 connected in this manner, a clinician or other administrator of the diagnostic assessment to be performed can operate computer 22 to store program instructions appropriate for the diagnostic procedure in an external memory unit 12. The programmed external memory unit 12 can be given to a patient or subject at the end of a clinical session or transmitted to the patient or subject by other appropriate means. The patient or subject can subsequently insert the programmed external memory unit 12 in a microprocessor-based unit 10 that is located at the patient's home or some other location at which the diagnostic procedure will be executed. Signals representative of the diagnostic information gathered during the procedure are stored in external memory unit 12 when microprocessor unit 10 implements the diagnostic assessment procedure. External memory unit 12 is then returned to the clinician, inserted into receptacle 38 and the clinician's computer 22 is used to retrieve the diagnostic information stored in the external memory unit 12. In situations in which program instructions and diagnostic results are stored internally in microprocessor-based unit 10 (i.e., without use of an external memory unit 12), the entire microprocessor-based unit can be taken to the clinician's office. Information relating to diagnostic assessment results can then be unloaded to the clinician's computer 22 and, if desired, program instructions can be downloaded to the microprocessor-based unit 10 for administering further diagnostic assessment.

As also is shown in FIG. 1, in most applications of the invention, an additional microprocessor-based unit 10 and audio/visual display unit 14 will be located at the clinician's office or other facility. In the arrangement shown in FIG. 1, the additional microprocessor-based unit 10 is directly connected to the clinician's computer 22 by an electrical cable 40 to allow signal transmission between the microprocessor-based unit and computer 22. Providing a microprocessor-based unit 10 and audio/visual display unit 14 at the clinician's location allows a patient or subject to be instructed in the use of the system and also allows the administration of diagnostic assessment procedures at the clinician's facility, if desired.

Figure 2:
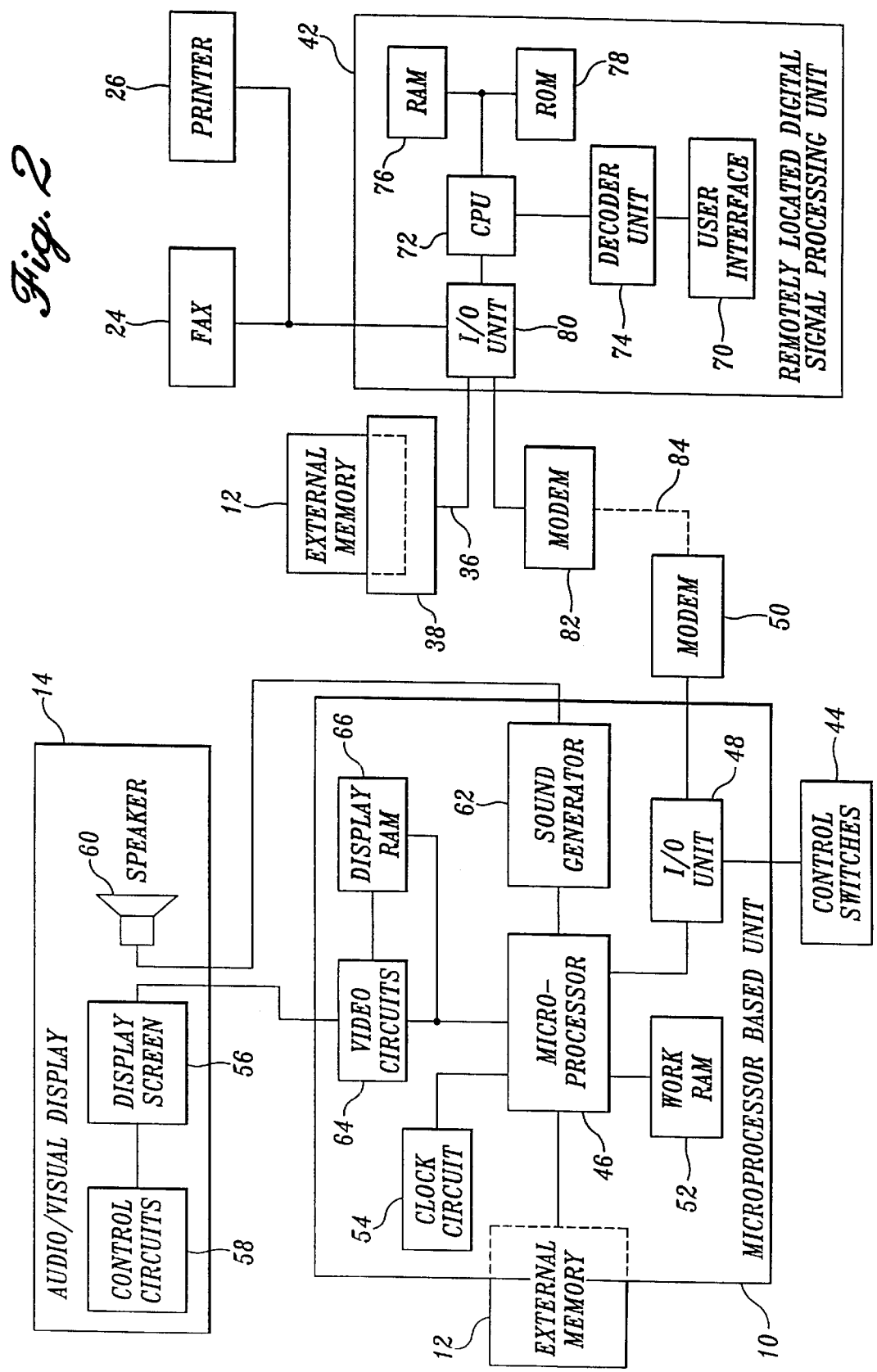
FIG. 2 is a block diagram illustrating in greater detail the basic structure of a microprocessor-based patient unit and a digital signal processor of a type that can be used within a clearinghouse or be used as a clinician's computer.

FIG. 2 depicts a more detailed block diagram of a microprocessor-based unit 10 that can be employed in the practice of the invention and an associated audio/visual display unit 14. Also shown in FIG. 2 is a basic block diagram of a remotely located digital signal processing system 42 which typifies the arrangement of clearinghouse 18 and computer 22 of FIG. 1.

As is indicated in FIG. 2, signals supplied by one or more control switches 44 are coupled to a microprocessor 46 of microprocessor-based unit 10 via an input/output circuit 48. Also interconnected with input/output unit 48 of microprocessor-based unit 10 is an external modem 50, which serves as data management unit 28 (FIG. 1) for the depicted arrangement. Although not indicated in FIG. 2, it will be understood by those skilled in the art that interconnections such as the connection shown between microprocessor 46 and input/output unit 48, generally include a data, address, and control bus.

With continued reference to microprocessor-based unit 10 of FIG. 2, the depicted microprocessor 46 is interconnected with the receptacle that receives an external memory unit 12 so that microprocessor 46 can access program instructions stored in external memory unit 12 and store diagnostic assessment results in external memory 12. As previously mentioned, program instructions can be provided to a microprocessor-based unit 10 via a digital signal communications system, instead of an external memory unit 12. In such arrangements, digital signals supplied by a system such as cable television or a digital communications can be coupled to microporcessor 46 via input/output unit 48 or other conventional signal processing arrangements.

In the arrangement of FIG. 2, a random access memory 52 is interconnected with and is used by microprocessor 46 to implement a desired diagnostic assessment procedure and perform any desired analysis of the gathered diagnostic data. In addition, random access memory 52 can be used for storing program instructions that are supplied to an embodiment of the invention that does not employ an external memory unit 12 (i.e., an embodiment in which program instructions are supplied via a digital signal communications system). A clock circuit 54 is provided to allow microprocessor 46 to store date and time signals in situations in which date and time tags are to be included with the gathered diagnostic data. Although not specifically shown in FIG. 2, microprocessor-based unit 10 generally includes an internal read-only memory for storing various program instructions and data that are not unique to a particular diagnostic assessment procedure or other application for the microprocessor-based unit 10.

The audio/visual display unit 14 that is shown in FIG. 2 corresponds to a video monitor that includes a display screen 56, control circuitry 58, and a speaker 60. In an arrangement of this type, microprocessor 46 of microprocessor-based unit 10 controls the operation of a sound generator 62 and video circuits 64 in accordance with the program instructions stored in external memory 12. A display random access memory 66 is used to store and format video signals which are coupled to display screen 56 of audio/visual display unit 14. Music, synthesized speech, and other sounds generated by sound generator 62 are coupled to speaker 60. Control circuit 58 includes the circuitry necessary for adjusting volume and display quality as well as the circuitry for driving the display screen. In other arrangements, a television set may be used as audio/visual display unit 14, with microprocessor-based unit 10 supplying an appropriate modulated rf signal or being connected to the television set video and audio inputs.

It will be recognized by those of ordinary skill in the art that a diagnostic tool that corresponds to microprocessor-based unit 10 of FIGS. 1 and 2 can be easily realized using conventional microprocessor design techniques and components. It also will be recognized that various commercially available devices can be adopted for use as a microprocessor-based unit 10 of this invention. In that regard, in the currently preferred embodiments of the invention, the microprocessor-based unit 10 is a compact video game system, with external memory unit 12 being configured to correspond to the type of game cartridge that is used with that particular video game system. In some arrangements of the invention, a handheld video game system such as the compact video game system marketed by Nintendo of America Inc. under the trademark "GAME BOY" can be used to realize, in unitary form, microprocessor-based unit 10, audio/visual display unit 14, and control switches 44 of the arrangement shown in FIG. 2. In other applications of the invention, a less compact video game system such as the "SUPER NINTENDO ENTERTAINMENT SYSTEM" or "NES" video game is used. In those situations, control switches 44 correspond to the video game controller and audio/visual display unit 14 is a conventional television set or video monitor. The less compact video game systems often are advantageous because the external memory unit (game cartridge) has greater memory capacity than the corresponding memory of handheld units; the microprocessor has superior processing capability; and relatively high-quality sound and graphics can be achieved.

Regardless of the type employed, there are many advantages to using a video game system in the practice of the invention. Of prime importance, video game systems enjoy widespread popularity and, hence, low cost. In many cases, the user of a diagnostic assessment system that is constructed in accordance with the invention may already own or have access to a video game system. In addition, video game systems are simple to use. Therefore, little time is required for instructing a patient or other system user in how to operate the system for performance of a particular diagnostic assessment. Even further, adapting a video game system for use with the invention provides a convenient way for realizing diagnostic assessment procedures that are presented in game-like format with animation or other graphics that provide motivation for all age groups while gathering needed diagnostic data. The cumulative effect is achievement of an unobtrusive test and diagnosis arrangement that is acceptable to patients and other subjects and can be used in many environments.

Referring again to FIG. 2, it can be recognized that the depicted remotely located digital signal processing unit 42 corresponds to a wide range of computational arrangements, including the clinician's computer 22 of FIG. 1 and the previously discussed, more complex, clearinghouse 18 of FIG. 1. In the arrangement depicted in FIG. 2, a user interface 70 is connected in signal communication with a central processor unit 72 via a decoder circuit 74. Random access memory 76 and read-only memory 78 are accessed by central processor unit 72 of digital signal processing unit 42 during execution of the various programs and procedures used in carrying out the invention. An input/output unit 80 acts under the direction of central processor unit 72 to provide signals to a facsimile unit 24 and printer 26. As also is indicated in FIG. 2, signals can be provided to central processor unit 72 via input/output unit 80 by a modem 82. In the arrangement shown, a communication link 84 interconnects modem 82 with modem 50 to thereby allow the depicted digital signal processing system to receive diagnostic test information from the depicted microprocessor-based unit 10. As also is indicated, input/output unit 80 is connected to a receptacle 38, which as was described relative to FIG. 1, allows the digital data processing system to access storage addresses within an external memory unit 12 that is connected to receptacle 38. As shall be described in more detail, an administration program that is executable by digital signal processing unit 42 includes a program module that allows program instructions to be stored in an external memory unit 12 to establish a desired diagnostic assessment procedure. Execution of another module of the administration program by digital signal processing unit 42 allows the retrieval of diagnostic test data stored in external memory unit 12 when a diagnostic assessment procedure was conducted (i.e., when a patient or user executed a diagnostic procedure in accordance with the procedure).

The currently preferred embodiments of the invention utilize a microprocessor-based unit 10 that corresponds to the previously mentioned SUPER NINTENDO ENTERTAINMENT SYSTEM, with the invention being realized for diagnostic assessment of Attention Deficit Disorder and Attention Deficit Hyperactivity Disorder. In the current realization of the invention, program instructions for a battery of separate tests that assess various aspects of a juvenile's attention are stored in external memory unit 12. Two basic types of tests are employed: tests that include a series of delayed reaction tasks and tests that include a series of continuous performance tasks. In the delayed reaction tasks, programmable microprocessor-based unit 10 operates to generate an audible and/or visual warning signal to alert the user that the microprocessor-based unit soon will produce an audible and/or visual trigger stimulus. When the trigger stimulus is generated, the patient or user activates a designated switch or control of microprocessor-based unit 10 (e.g., a switch or control included in control switches 44 of FIG. 2). In current practice, the clinician or other administrator of the diagnostic assessment procedure can select one or more audio delayed reaction tests and/one or more video delayed reaction tests when establishing a battery of tests for a particular patient or user. As shall be described relative to FIGS. 6–11, the clinician establishes the battery of tests by executing a computer program, which also allows the clinician or administrator to establish the sequence in which various tests will be administered and, for each audio or visual delayed reaction test, select both the number of trigger stimuli to be generated and a time delay range. The time delay range establishes the upper and lower bounds of the delay between warning stimuli and trigger stimuli. The specific delay between a particular warning stimulus and its associated trigger stimulus is selected randomly by microprocessor-based unit 10 when the delayed reaction test is conducted.

Each time that microprocessor-based unit 10 generates a trigger stimulus, a timer (e.g., clock circuit 54 of FIG. 2) is activated. If the patient or user does not activate the appropriate switch or control within a predetermined time interval, a digital signal is stored indicating a failure to respond. On the other hand, if the patient or user responds, a digital signal is stored indicating the user's reaction time (i.e., the time period between the occurrence of a trigger stimulus and the patient's reaction). Since a series of delayed reaction tasks is used in each audio or visual delayed reaction test, the stored data that are accumulated during the diagnostic assessment will allow later analysis to determine various measures that relate to the patient's degree of attention. For example, measures that can be important include the user's fastest reaction time, his or her mean reaction time, and the standard deviation of reaction times. In addition, the difference between the results for audio and visual delayed reaction tasks may also be considered. For example, young children tend to respond more quickly to audio trigger stimuli than video trigger stimuli. Thus, the relationship between the results of audio and video delayed reaction tests for a patient may provide some insight as to that patient's relative deficit or development of both auditory and visual attention skills.

Figure 3:
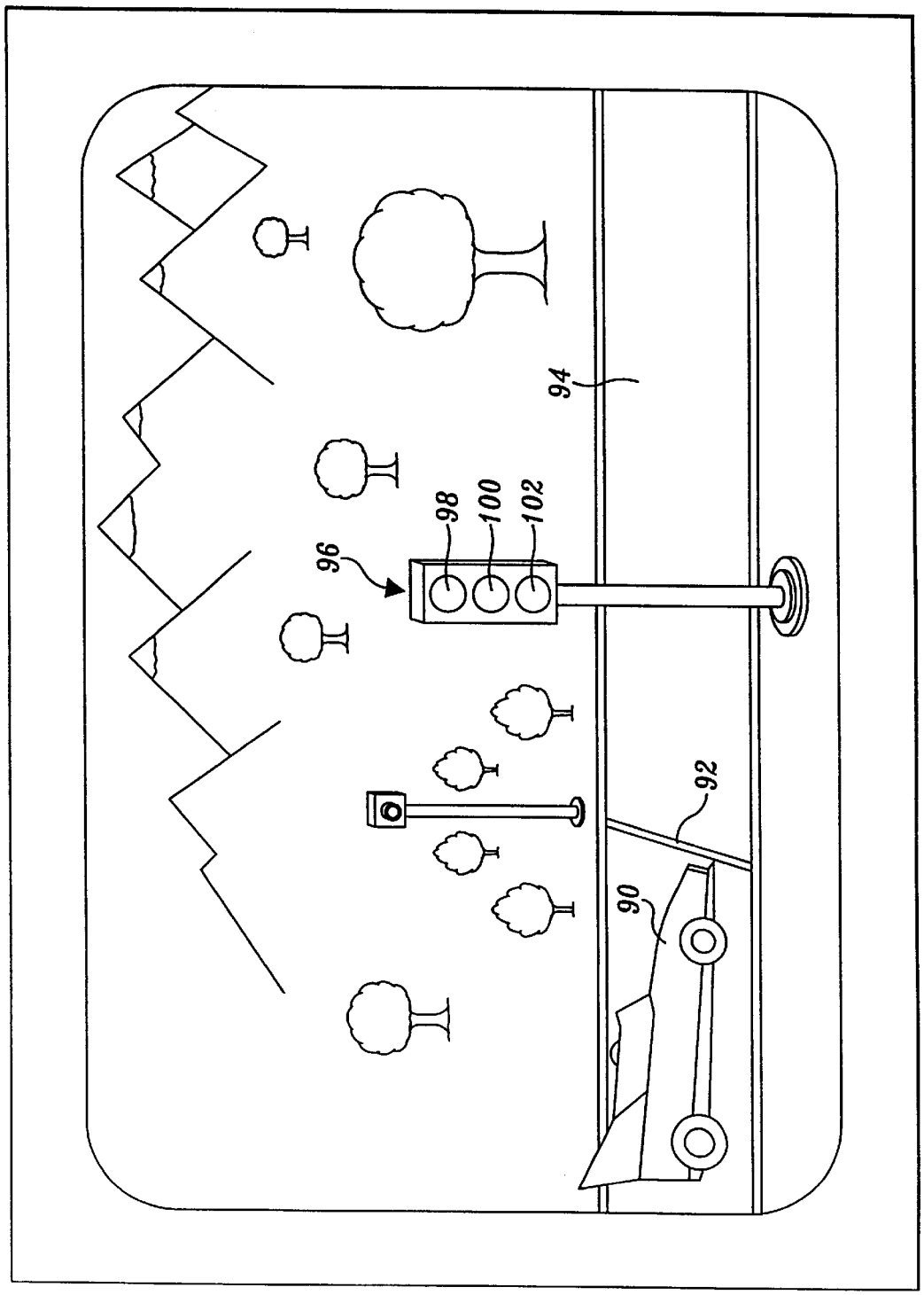
FIG. 3 illustrates a graphic display suitable for use when a microprocessor-based patient unit administers a delayed reaction tests in an embodiment of the invention that is configured for diagnostic measurements relating to Attention Deficit Hyperactivity Disorder or Attention Deficit Disorder.

In the currently preferred realizations of embodiments for use in diagnostic assessment of Attention Deficit Hyperactivity Disorder and Attention Deficit Disorder, external memory unit 12 is programmed to cause microprocessor unit 10 to generate a display of the type shown in simplified form in FIG. 3. In the display of FIG. 3, a car 90 is positioned at a starting line 92 on a roadway or racetrack 94. A traffic signal 96, having a red light 98, an amber light 100, and a green light 102, is prominently displayed. As each visual delayed reaction task is generated, microprocessor-based unit 10 causes sequential illumination of red light 98, amber light 100, and green light 102. Amber light 100 serves as the warning stimulus, with green light 102 providing a trigger stimulus after a randomly generated time delay that is within the time delay range that was established when the visual delayed reaction test being executed was established by the clinician or the administrator having control over the diagnostic testing.

During the audio delayed reaction tests, the three lights of traffic light 100 in FIG. 3 are extinguished and program instructions that are stored in external memory unit 12 result in generation of suitable audio warning and trigger stimuli by sound generator 62 of FIG. 2. In arrangements having sufficient memory and sound generation capability, the words "ready . . . set . . . go" are used, with the time interval between "set" and "go" being a random value within the range of values selected when a clinician established the diagnostic procedure. Two tones that are clearly distinct from one another also can be used for the warning and trigger stimuli.

The currently preferred realizations of embodiments of the invention that are directed to diagnostic assessment of Attention Deficit Hyperactivity Disorder and Attention Deficit Disorder provide for both visual and audible continuous performance tests. In each test a sequence or series of events occurs for which the patient or user is to respond by activating a predetermined switch or control such as the control switches 44 in the arrangement of FIG. 2. The continuous performance test used in the currently preferred embodiments of the invention are performance-paced in that the interstimulus stimulus interval (i.e., the time that elapses between consecutive stimuli) is reduced by a predetermined amount each time a correct response is made and is increased by the same or a different predetermined amount if an improper response occurs (i.e., the user responds to a non-target stimulus or fails to respond to a target stimulus).

Figure 4:
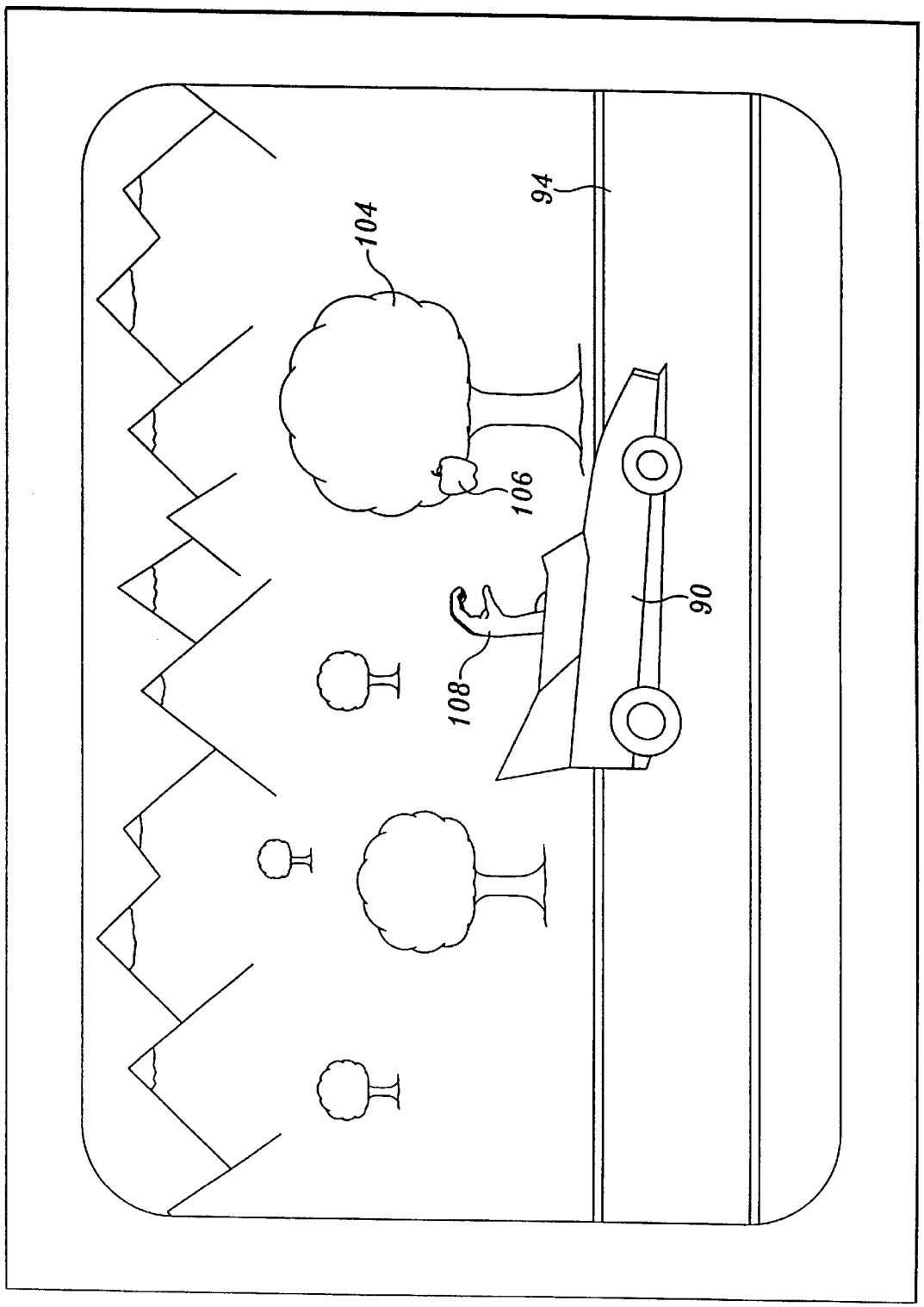
FIG. 4 illustrates a graphic display suitable for use when a microprocessor-based patient unit administers continuous performance tests in an embodiment of the invention that is configured and programmed for diagnostic measurement relating to Attention Deficit Hyperactivity Disorder and Attention Deficit Disorder.

The video display for the continuous performance tests of the currently preferred embodiments is indicated in FIG. 4. In FIG. 4, the car 90 that is used in the above-discussed delayed reaction tests is shown traveling along a roadway 94. Periodically, the car 90 approaches a tree 104, which is positioned along side roadway 94. As car 90 approaches a tree 104, various types of fruit (oranges, apples, lemons, and grapes) will appear, hanging downwardly from a branch of the tree. The object is for the patient or user to respond to a specified type of fruit only (e.g., apple 106 in FIG. 4) by depressing a selected switch such as one of the switches of control switches 44 in FIG. 2. When the appropriate switch is pressed, a hand and arm 108 extend upwardly from car 90 to capture the fruit. As previously noted, with each correct response, the interstimulus interval is decreased (i.e., the car 90 appears to travel at a higher rate of speed) and with each incorrect response or failure to respond, the interstimulus interval is increased (car 90 appears to travel slower).

In the audio continuous performance tests of the referenced realizations of the invention, the display shows car 90 traveling at night, with only a portion of roadway 94 being illuminated by the car's headlights. Each time the car approaches a darkened tree 104, a low-frequency radar-like "beep" is heard if the tree does not bear the desired fruit (apple 106 in FIG. 4). When the proper fruit is present, a high-pitched radar-like beep is emitted.

Figure 5:
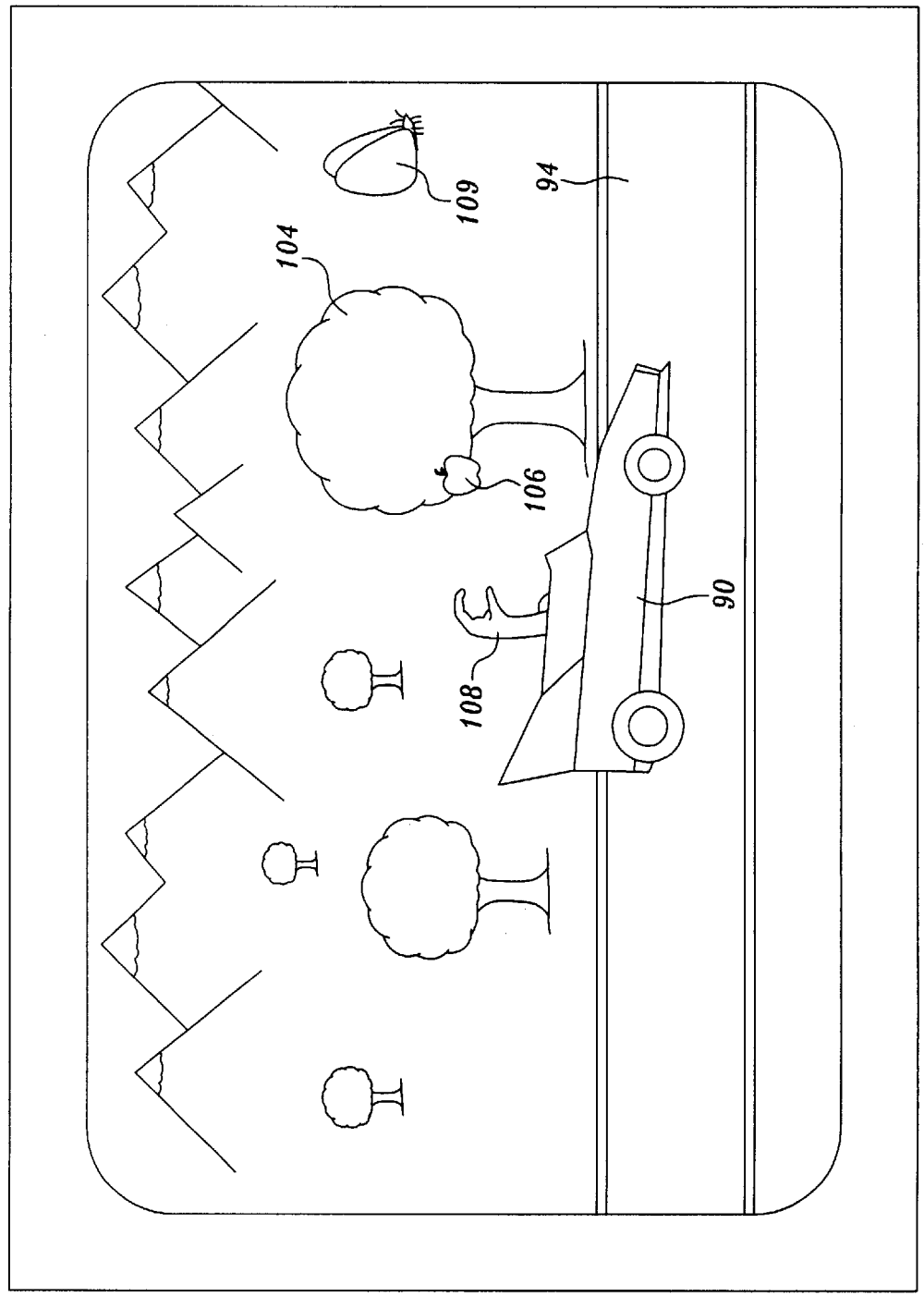
FIG. 5 illustrates a graphic display suitable for use when a microprocessor-based patient unit administers continuous performance tests that also include visual distractions in an embodiment of the invention that is configured and programmed for diagnostic measurement relative to Attention Deficit Hyperactivity Disorder and Attention Deficit Disorder.

Embodiments of the invention for diagnostic assessment for Attention Deficit Hyperactivity Disorder and Attention Deficit Disorder can also include programming for conduction of continuous performance tests that include distractions. For example, as is shown in FIG. 5, a fluttering butterfly 109 or other moving object such as a hopping frog or flying saucer can be generated in the peripheral region of the video display to provide a measure of the patient's degree of distractibility. During audio continuous performance tests synthesized voice signals such as "Now!" or "Go!" can be generated by microprocessor-based unit 10. In situations in which synthesized voice is beyond the capability of the sound generator being used, the microprocessor-based unit 10 can supply various distractive sounds or noises.

When the battery of diagnostic assessments is established by a clinician, program instructions can be stored in external memory unit 12 (or otherwise provided to a microprocessor-based unit) to determine the number of continuous performance tests to be performed and the type of each test (i.e., video without distractions; video with distractions; audio without distractions; and, audio with distractions). The sequence of the tests, both with respect to one another and with respect to the previously discussed delayed reaction tests, is also determined by the clinician. For each continuous performance test, the clinician can select the total number of target and non-target stimuli to be presented; the test duration; and the minimum stimulus duration (which is typically set at around 100 milliseconds). Diagnostic measures that are recorded in external memory unit 12 during conduction of continuous performance tests include: the number of target stimuli correctly identified (i.e., captured); the number of target stimuli for which the user failed to react (missed stimuli); the number of non-target stimuli for which there was a response; the number of times the button or switch was activated after a stimulus passed (late hits); and the final interstimulus interval (and/or the minimum interstimulus interval attained during the test).

As was described relative to FIGS. 1 and 2, program instructions for establishing the diagnostic assessment procedure (e.g., storing suitable program instructions in external memory 12) and retrieval of signals representative of the diagnostic measures gathered during diagnostic testing (e.g., accessing information stored in external memory 12) are performed by executing an administrator program with the clinician's computer (22 in FIG. 1; digital signal processing unit 42 in FIG. 2). When the administrator program of the current realizations of the invention is executed, a main menu screen is displayed, allowing the clinician to select menu items that include: the opening of a new file (i.e., establishing a diagnostic assessment procedure for a new patient or subject); opening an existing file; saving a file (storing a diagnostic assessment configuration in memory of the clinician's computer); closing a file; and producing the diagnostic assessment procedure (i.e., storing the appropriate program instructions in an external memory 12 or, alternatively, initiating execution of a diagnostic assessment procedure with a microprocessor-based unit 10 that is directly connected to the clinician's computer (FIG. 2).

Figure 6:
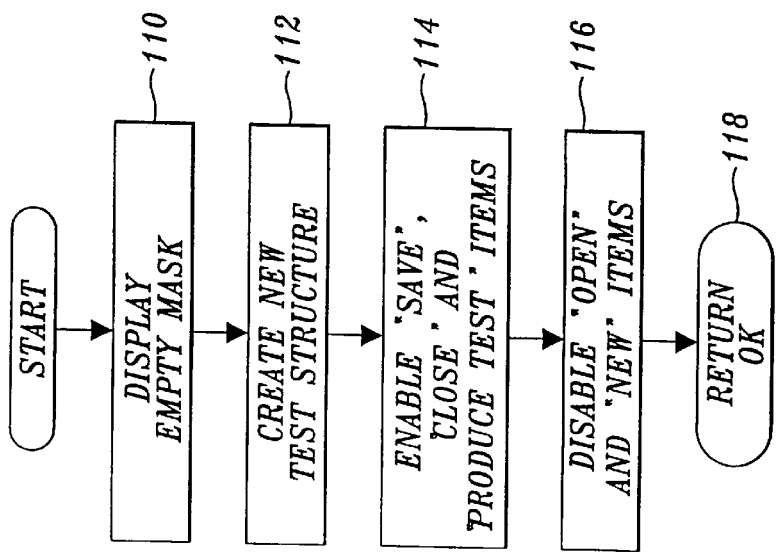

The sequence of steps that is executed when a new file is opened during execution of the administrator program is shown in FIG. 6. As is indicated at block 1 10 the first step of opening a new file is the display of a "mask," i.e., a form that includes empty fields for insertion of information such as the name of the patient or subject, age, sex, grade or educational level, date on which the test is to be performed, name of attending physician or clinician; and the identity of the person establishing the diagnostic assessment procedure.

The next step of establishing a new file is indicated at block 112 and consists of creating the desired diagnostic assessment procedure. In this step, a set-up screen is displayed that allows the clinician or test administrator to establish a desired battery of the previously described audio and visual delayed reaction tests and the previously described audio and visual continued performance tests (both with and without distractions). The tests can be selected in any sequence and, if desired, a particular type of test can be repeated without intervening execution of a different type of test. Further, in the currently preferred realizations of the invention, a short training procedure is available for both delayed reaction testing and continuous performance testing. In most cases, the clinician or administrator will include one or both of the training procedures in the diagnostic assessment procedure.

The set-up screen also includes provision for the clinician or administrator to select the various previously mentioned delayed reaction test parameters and continuous performance test parameters. Specifically, the clinician can select the delay range that will determine the upper and lower limits of the random time delay between a warning stimulus and a trigger stimulus in the delayed reaction tests and can also set the number of trigger stimuli that will occur during each delayed reaction test. With respect to each continuous performance test, the set-up screen allows the clinician to set the duration of each test, the percentage of target stimuli (i.e., the mix of non-target and target stimuli), the amount by which the interstimulus interval decreases each time a patient or subject captures a target stimulus; the amount by which the interstimulus interval increases when the patient misses; and the type of target stimulus to be used (e.g., apples, grapes, lemons, or oranges).

Once the diagnostic assessment procedure has been established for a patient or subject, the sequence for establishing a new file causes the "save," "close," and "produce test" sequences of the administrator program to be enabled (indicated at block 114) and disables the "open" and "new" sequences of the administrator program (see block 116). As is indicated at block 118 in FIG. 6, the sequence then returns to the menu screen. Since the "open" and "new" sequences have been disabled, those menu items are preferably at least partially blanked out or otherwise indicated as not being available for selection.

Figure 7:
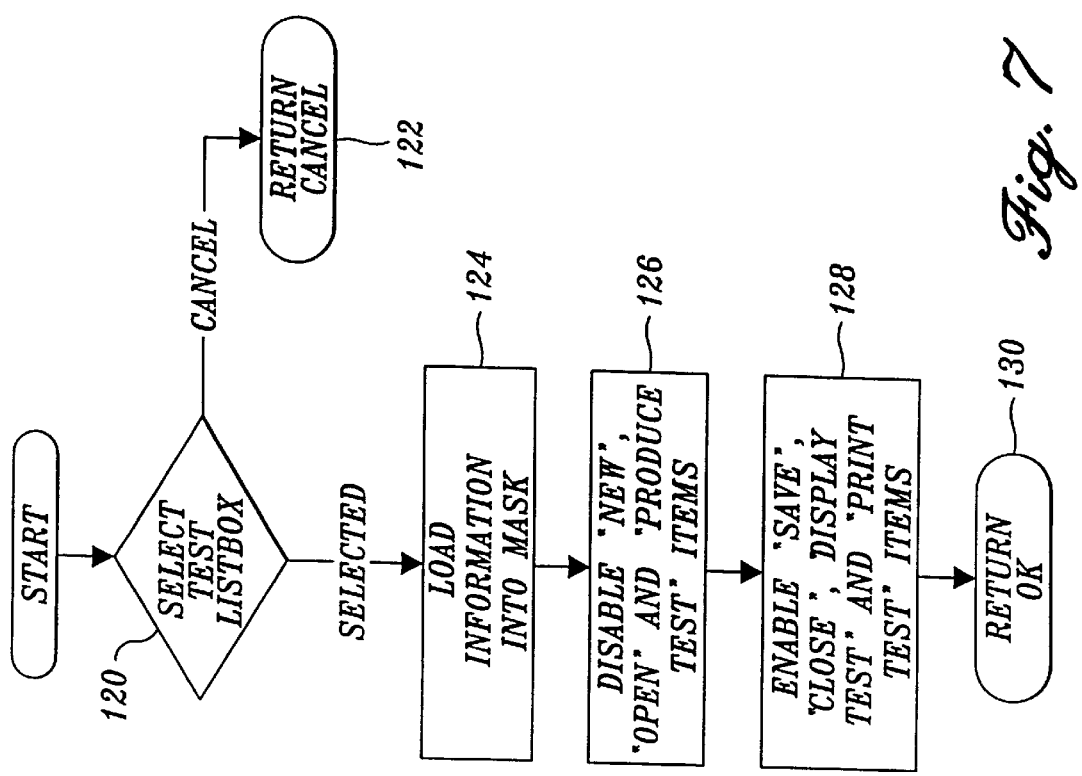
FIGS. 6–11 are sequence diagrams that illustrate operation of a clinician's computer during periods of time in which the computer is used to establish a battery of tests to be administered by the microprocessor-based unit; is used to supply program instructions to the microprocessor-based unit that will result in the desired psychological diagnostic testing; and, is used to retrieve diagnostic measurements obtained by the microprocessor-based unit during the administration of the diagnostic test.

When the administrator program is initiated, the clinician can select the "open file" menu item as an alternative to the "new file" item. As is indicated in FIG. 7, the sequence that is executed when the "open file" menu item is selected begins with the display with a list of existing files (e.g., patient names or identification numbers), which is indicated at block 120. Also displayed is an option that allows the clinician or administrator to cancel the sequence for opening a file. If selected, the option for canceling the sequence returns the screen display to a display of the main menu (indicated at block 122). On the other hand, if the clinician or administrator selects a particular patient, the information about the patient and the battery of tests and test parameters that was recorded during the new file procedure is displayed (indicated at block 124). As is shown at block 126, the administrator program then sequences to disable menu items that would otherwise allow the opening of a new or different. The menu item that allows the production of a diagnostic test routine (such as the loading of an external memory unit 12 with program instructions) also is disabled. As is indicated at block 128, menu items for saving a file, closing a file, and for displaying or printing test results that were stored when the diagnostic assessment procedure for that patient was conducted or enabled. The system then returns to displaying the menu with the enabled menu items being displayed in a manner that distinguishes those menu items from the disabled menu items (indicated at block 130).

Figure 8:
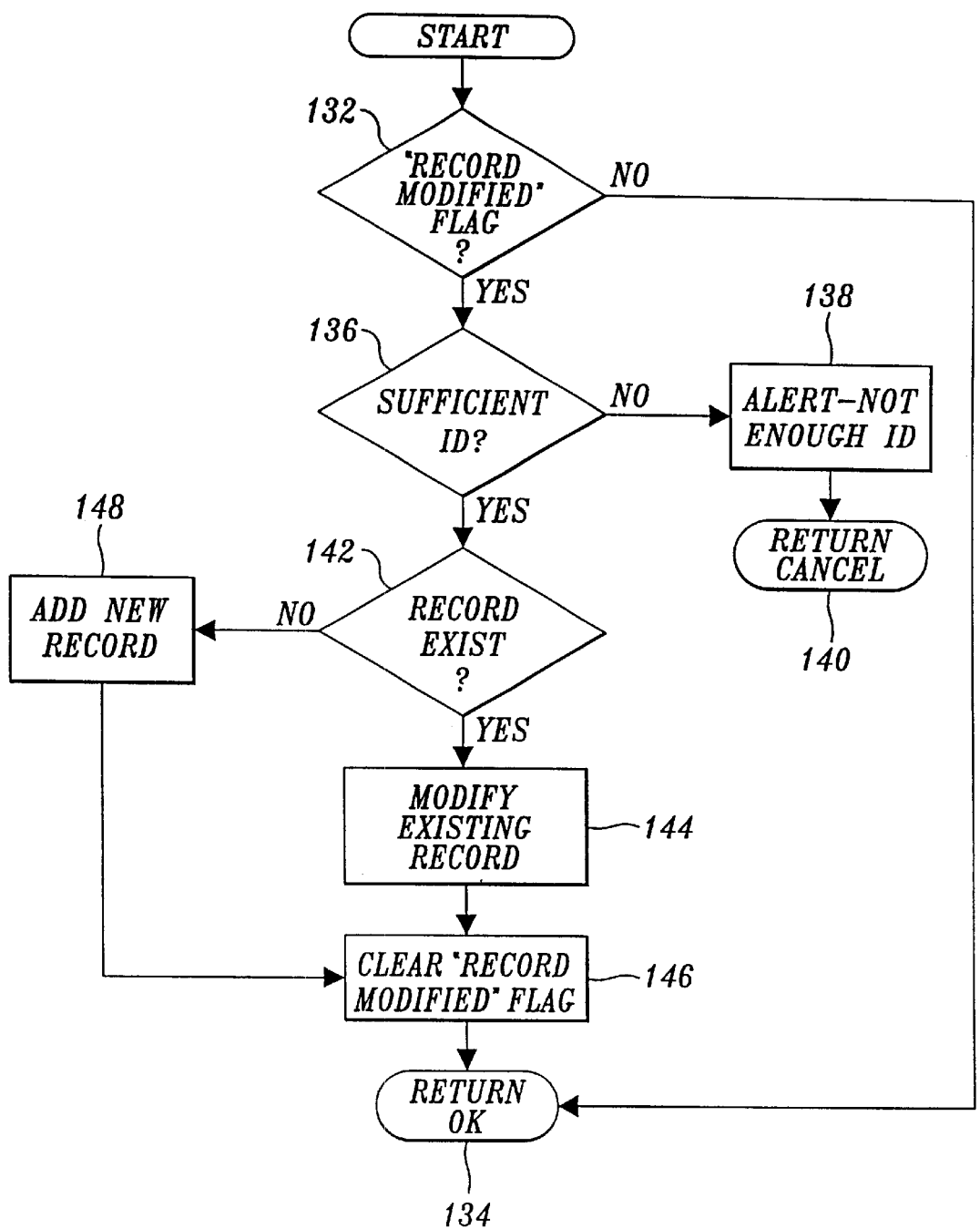

The sequence that is executed when the administrator program is used to save a patient file is shown in FIG. 8 and begins with a determination of whether a "record modified" is set (block 132). The record modified flag is a field in the data record for each patient and is set whenever that patient's file is opened and modified by adding new information, or changing information that was previously entered. If the record modified flag is not set, the sequence shown in FIG. 8 is terminated and the system display returns to the selection menu (indicated at block 134). On the other hand, if the record modified flag is set, a determination is made as to whether sufficient patient identification information is included in the patient file or record being processed (indicated at decision block 136). In the event of insufficient identification a warning message is displayed (block 138). The sequence for saving the file is cancelled and the display returns to the main menu (indicated at block 140).

When sufficient patient identification is included in the record being processed, the administrator program determines whether the record already exists (decision block 142). As is shown at block 144, an existing file is modified in accordance with information included in the file being saved. Next, the record modified flag is cleared (block 146); and the system display is returned to the main menu (block 134). However, if the file being processed does not already exist, a new record is stored in system memory (block 148); the record modified flag is cleared (block 146); and the system display is returned to the main menu (block 134).

Figure 9:
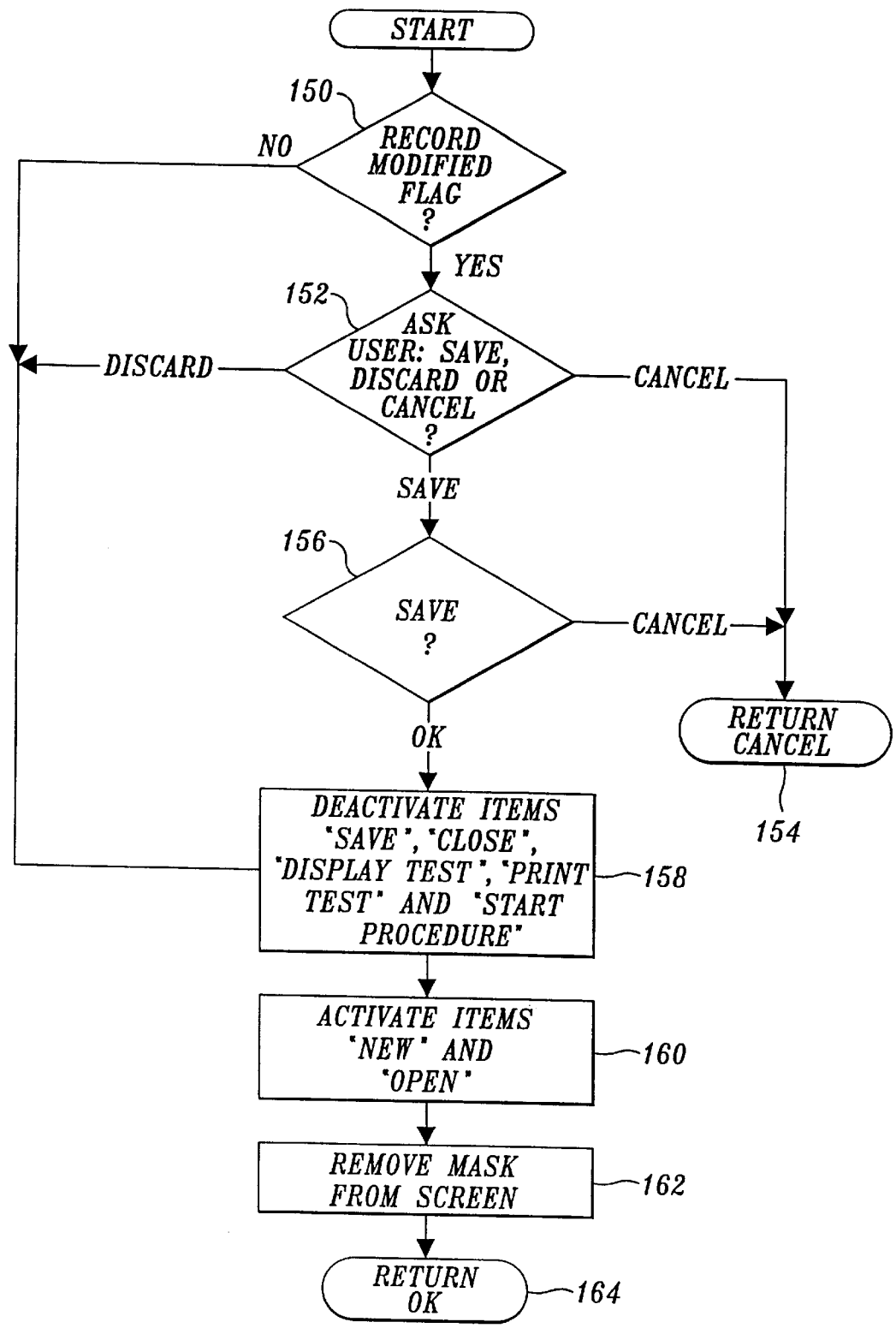

As is shown in FIG. 9, the sequence by which the administrator program closes a previously opened patient record begins with a determination of whether the record modifier flag is set (indicated at decision block 150). If the record has been modified, the clinician or administrator executing the program is prompted to specify whether the modified record should be saved, discarded, or whether the sequence to close the record should be canceled (indicated at block 152). As is indicated at block 156, if the modified record is to be saved, the above-discussed sequence for saving the record is executed. If the user determines cancel (see decision block 152) and/or the modified record is not to be saved (see decision block 156), a return cancel occurs (see block 154), similar to that described for block 122 in FIG. 7.

A determination at decision block 150 that the record has not been modified causes deactivation of the menu items for saving a file or record, closing a file, and for displaying and printing test results. The menu item that allows storage of program instructions in an external memory 12 or the alternative administration of a diagnostic assessment procedure with a microprocessor-based unit 10 that is connected to the clinician's computer is also disabled (all indicated at block 158 in FIG. 9). As is shown in FIG. 9, these menu items also are disabled after saving a modified file (i.e., the completion of the operation indicated at block 156) and, in addition, upon executing an instruction to discard a modified record (shown at block 152). As is indicated at block 160, once the specified menu items have been disabled, the menu items for establishing a new file and for opening an existing file are enabled (block 160); the record is removed from the display screen (block 162); and the main menu is displayed (block 164).

Figure 10:
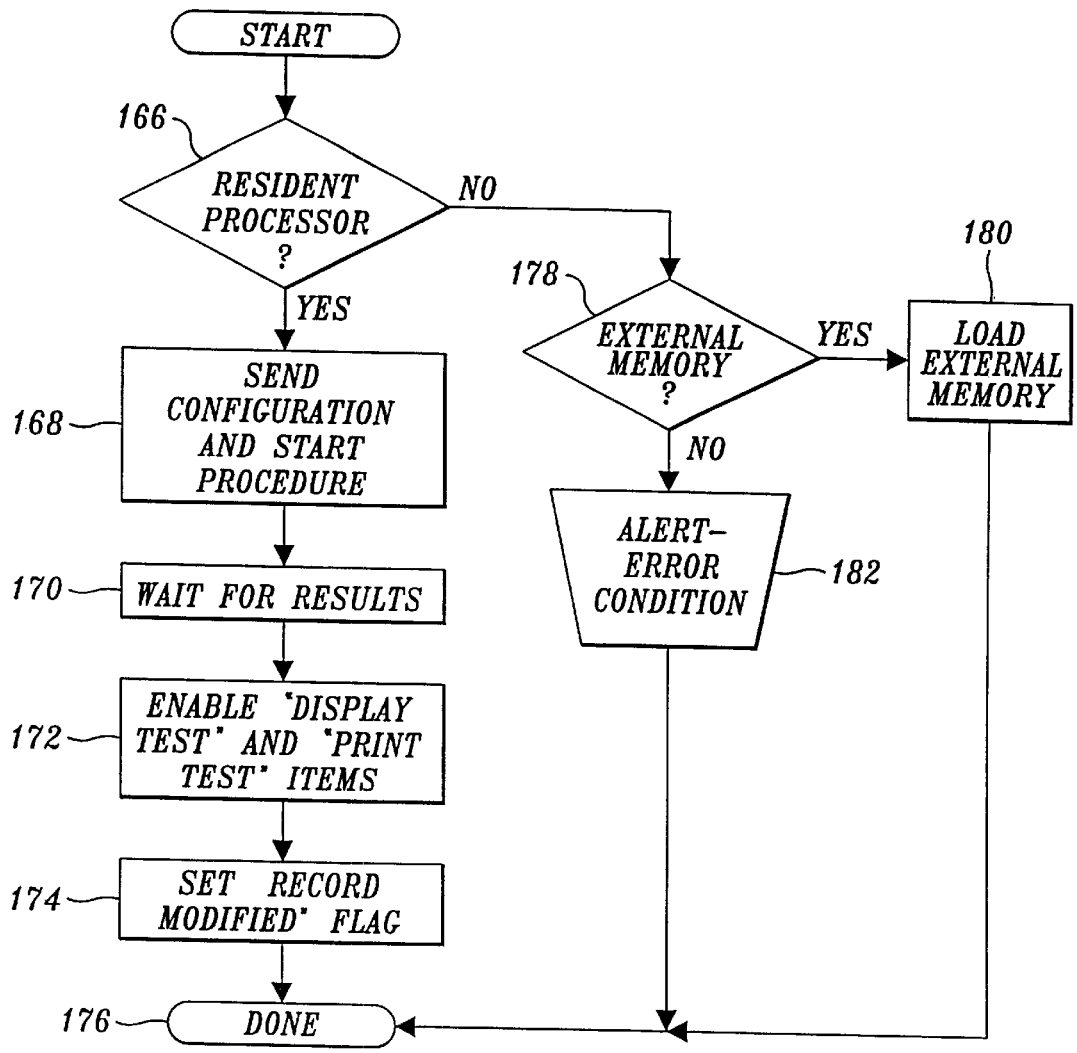

The sequence that is executed during the administrator program to load desired program instructions into an external memory unit 12 or, alternatively, initiate a diagnostic assessment procedure with a microprocessor-based unit 10 that is electrically connected to the clinician's computer is shown in FIG. 10. As is indicated at decision block 166, the sequence begins with a determination of whether a microprocessor-based unit 10 is both connected to the clinician's computer and is turned on. If a microprocessor-based unit is both connected and active, the program instructions required to configure the microprocessor for the test specified in the currently open patient file are transferred to the microprocessor-based unit (block 168). The sequence then remains in a "wait" state until the microprocessor 10 signals that the diagnostic test results are available (block 170). Once the test results are available and stored in memory, the menu items for displaying test results and printing test results are enabled (block 172); the previously discussed record modified flag is set (block 174); and the system display returns to the main menu (block 176).

When a microprocessor unit 10 that is electrically connected with the clinician's computer is not turned on (determined at block 166), a determination is made at block 178 as to whether an external memory unit 12 is to be loaded with program instructions (e.g., whether an external memory unit 12 is present in receptacle 38 of the arrangements shown in FIGS. 1 and 2). If an external memory unit 12 is not present, a message is displayed indicating that an error condition has been encountered (block 182) and the administrator program sequences to the main menu screen (block 176). If an external memory unit 12 is present, the program instructions for establishing a diagnostic assessment procedure for the open patient file are loaded into the external memory unit 12 for subsequent use by the patient (see block 180).

Figure 11:
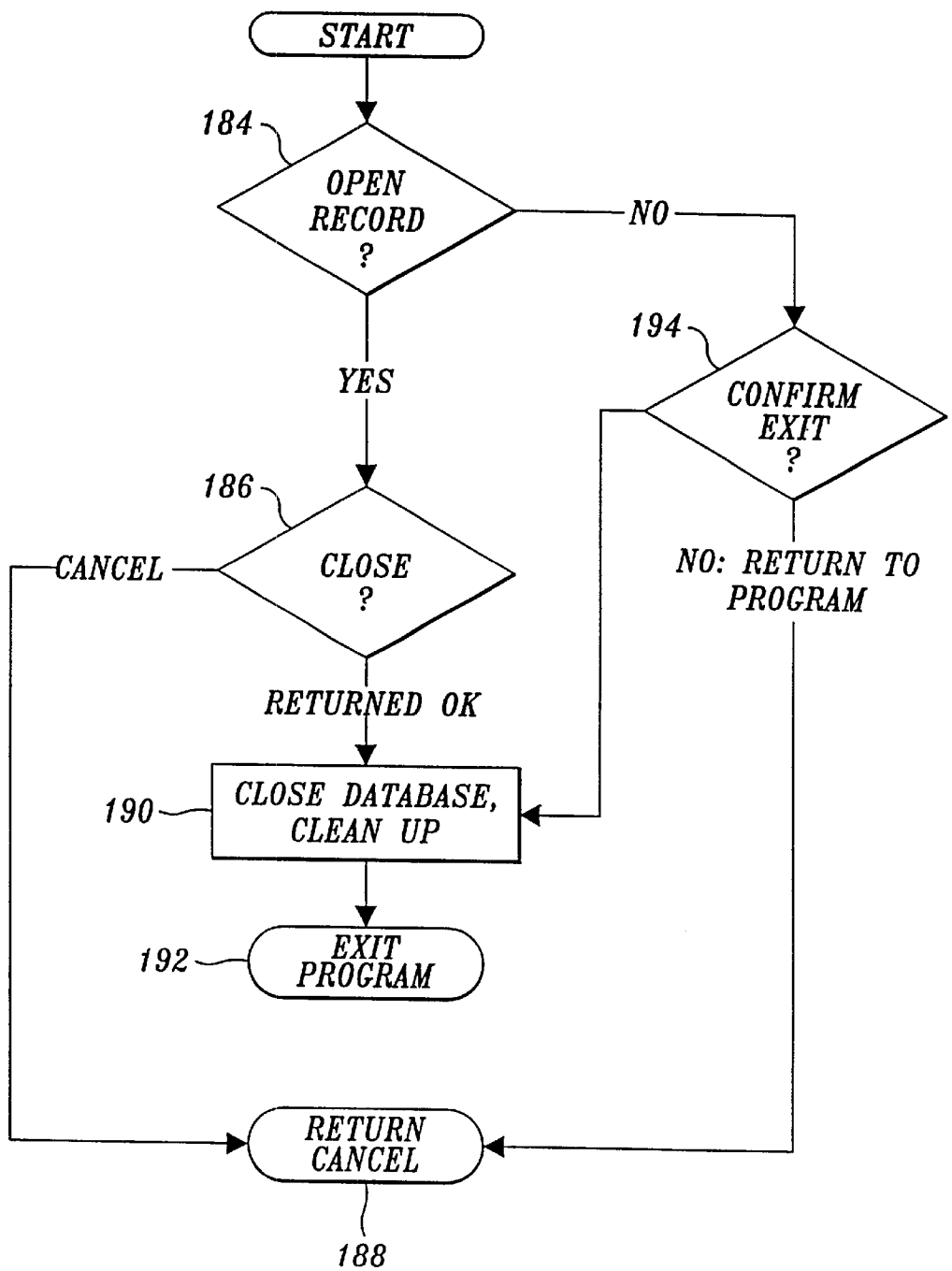

Referring to FIG. 11, the sequence by which the clinician or administrator exits the administrator program begins with the determination as to whether a patient file or record is open (decision block 184). If an open patient file or record is detected, the sequence for closing the file that was discussed relative to FIG. 9 is executed (indicated at block 186). If the sequence for closing the file is cancelled prior to completion, the sequence for exiting the administrator program is cancelled and the main menu is displayed (indicated at block 188). Successful completion of the sequence for closing an open file results in execution of "housekeeping" routines that close the database that stores test results and, in addition, perform memory cleanup operations (indicated at block 190); and the administrator program is removed from active memory (indicated at block 192).

If no record is open when the exit sequence is executed (determined at block 184), the clinician is prompted to confirm whether an exit from the administrator program is to be made (indicated at block 194). If the exit command is verified, the database of test results is closed and memory cleanup accomplished (block 190), with subsequent exit from the administrator program (block 192). In the event exit is not to be made, the main menu is again displayed (block 188).

While the preferred embodiment of the invention has been illustrated and described, it will be appreciated that various changes can be made therein without departing from the spirit and scope of the invention. As previously mentioned, the invention can be embodied in various ways to provide a microprocessor-based unit with program instructions that cause the microprocessor-based unit to operate in a manner suitable for the assessment of various psychological conditions. For example, in assessing and treating habitual smoking or addiction to nicotine, a microprocessor-based unit (e.g., video game system) can be programmed to present a game-like presentation that may or may not directly relate to smoking. Such a unit can be given to a user with instructions to "play" the game-like presentation each time the user has an urge to smoke over a predetermined period such as three weeks. At the end of the prescribed period, the clinician can access the stored information and based on computer assisted analysis of the retrieved data can determine the nature, frequency and severity of the user's habit or addiction, as well as the motivation or stimulus that triggers an urge to smoke. Based on that information, an informed decision can be reached as to whether the user of the system (e.g., patient) is likely to respond to behavioral therapy or whether chemical replacement therapy or a combination of the two therapies should be used. Various other addictions and behavioral patterns can be assessed in similar fashion.

As another example of the manner in which the invention can be embodied, a series of interactive assessment sessions for conditions such as depression or anxiety can be presented via interactive cable television to a wide audience. In such an arrangement, the patient or subject is enrolled in the sessions by a psychiatrist or other healthcare professional. The patient or user tunes the interactive television system to a predetermined channel at a predetermined time and enters a personal identification code via a microprocessor-based unit that is connected for receiving and sending signals via the interactive television system. Program instructions are then provided to the microprocessor-based unit via the interactive television system and the patient or user responds to various stimuli during the televised diagnostic assessment section. As is the case with other arrangements of the invention, the televised assessment session can be in a game-like format or other presentation that is unobtrusive. Diagnostic information gathered during the session can be provided to the clinician in one of the several ways discussed with respect to FIGS. 1 and 2. By analyzing the diagnostic assessment data gathered during the interactive assessment sessions, the psychiatrist or other healthcare professional can make a better informed decision as to the need for clinical therapy and/or medication than can be made based only on traditional clinical sessions.

What is claimed is:

1. A method of assessing the psychological condition of a human patient comprising:

setting at least one test to be executed by a patient;

executing the at least one set test;

recording patient responses to the executed test;

analyzing the recorded patient responses; and wherein the at least one set test is an animated sequence that includes a sequence of delayed reaction tasks, wherein a delayed reaction task includes at least one warning stimulus separated in time from a target stimulus, said at least one warning stimulus being generated to alert the patient of generation of the target stimulus, but not being intended to stimulate response by the patient, and wherein said time separation is automatically changed according to said recorded patient responses to the warning and target stimuli.

2. A method of assessing the psychological condition of a human patient comprising:

setting at least one test to be executed by a patient;

executing the at least one set test;

recording patient responses to the executed test;

analyzing the recorded patient responses; and wherein the at least one test set by a clinician is an animated sequence that includes a sequence of continuous performance tasks, wherein a delayed continuous performance task includes two or more target stimuli separated in time, said target stimuli being generated to stimulate response by the patient, and wherein said time period between target stimuli is automatically changed according to patient responses to the target stimuli.

\* \* \* \* \*